(12) United States Patent
Gibson et al.

(10) Patent No.: US 9,149,452 B2
(45) Date of Patent: Oct. 6, 2015

(54) METHODS AND COMPOSITIONS FOR PROMOTING THE NEUROLOGICAL DEVELOPMENT OF AN INFANT

(75) Inventors: Robert Gibson, Port Willunga (AU); Maria Makrides, Norwood (AU)

(73) Assignee: WOMEN'S & CHILDREN'S HEALTH RESEARCH INSTITUTE INC., North Adelaide (AU)

( * ) Notice: Subject to any disclaimer, the term of this patent is extended or adjusted under 35 U.S.C. 154(b) by 179 days.

(21) Appl. No.: 12/761,730

(22) Filed: Apr. 16, 2010

(65) Prior Publication Data

US 2010/0267830 A1 Oct. 21, 2010

Related U.S. Application Data

(60) Provisional application No. 61/170,685, filed on Apr. 20, 2009.

(51) Int. Cl.
*A61K 31/202* (2006.01)

(52) U.S. Cl.
CPC .................................... *A61K 31/202* (2013.01)

(58) Field of Classification Search
CPC ..................................................... A61K 31/202
See application file for complete search history.

(56) References Cited

U.S. PATENT DOCUMENTS

| | | | |
|---|---|---|---|
| 6,036,992 A * | 3/2000 | Borror et al. ................... | 426/662 |
| 8,053,471 B2 | 11/2011 | Stahl et al. | |
| 2002/0004527 A1 | 1/2002 | Auestad et al. | |
| 2002/0031576 A1 | 3/2002 | Barrett-Reis et al. | |
| 2004/0143013 A1 | 7/2004 | Schade et al. | |
| 2008/0003330 A1 | 1/2008 | Rueda et al. | |
| 2008/0269330 A1 | 10/2008 | Stahl et al. | |
| 2008/0286416 A1 | 11/2008 | Euber et al. | |
| 2010/0234286 A1 | 9/2010 | Georgi et al. | |

FOREIGN PATENT DOCUMENTS

WO 0178530 A2 10/2001

OTHER PUBLICATIONS

American Pregnancy Association. http://www.americanpregnancy.org/firstyearoflife/whatsinbreastmilk.html, accessed Apr. 16, 2012.*
Babycenter. http://www.babycenter.com/average-fetal-length-weight-chart. accessed Apr. 16, 2012.*
Koletzko B, Agostoni C, Carlson SE, Clandinin T, Hornstra G, Neuringer M, Uauy R, Yamashiro Y, Willatts P. Long chain polyunsaturated fatty acids (LC-PUFA) and perinatal development. Acta Paediatr. Apr. 2001;90(4):460-4.*
Mayes C, Burdge GC, Bingham A, Murphy JL, Tubman R, Wootton SA. Variation in [U-13C] alpha linolenic acid absorption, beta-oxidation and conversion to docosahexaenoic acid in the pre-term infant fed a DHA-enriched formula. Pediatr Res. Feb. 2006;59(2):271-5.*
Mayo Clinic. http://www.mayoclinic.com/health/breast-feeding/FL00105. accessed Apr. 16, 2012.*
Smithers LG, Gibson RA, McPhee A, Makrides M. Effect of two doses of docosahexaenoic acid (DHA) in the diet of preterm infants on infant fatty acid status: results from the DINO trial. Prostaglandins Leukot Essent Fatty Acids. Sep.-Nov. 2008;79(3-5):141-6. Epub Oct. 23, 2008.*
Yuhas R, Pramuk K, Lien EL. Human milk fatty acid composition from nine countries varies most in DHA. Lipids. Sep. 2006;41(9):851-8.*
Innis SM, Friesen RW. Essential n-3 fatty acids in pregnant women and early visual acuity maturation in term infants. Am J Clin Nutr. Mar. 2008;87(3):548-57.*
Makrides M., Neumann M.A., Gibson R.A. Effect of maternal docosahexaenoic acid (DHA) supplementation on breast milk composition. Eur J Clin Nutr. 1996; 50(6): 352-357.
Liang K-Y., Zeger S.L. Longitudinal data analysis using generalized linear models. Biometrika. 1986; 73(1): 13-22.
Lucas A., Morley R., Cole T.J., Lister G., Leeson-Payne C. Breast milk and subsequent intelligence quotient in children born preterm. Lancet. 1992; 339(8788): 261-264.
Frankenburg W.K., Coons C.E. Home Screening Questionnaire: its validity in assessing home environment. J Pediatr. 1986; 108(4): 624-626.
L. G. Smithers et al. "Effect of two doses of docosahexaenoic acid (DHA) in the diet of preterm infants on infant fatty acid status: Results from the DINO trial" Prostaglandins, Leukotrienes and Essential Fatty Acds, vol. 79, (2008) pp. 141-146.
Maria Makrides et al. "Neurodevelopmental Outcomes of Preterm Infants Fed High-Dose Docosahexaenoic Acid-A Randomized Controlled Trial" Downloaded from www.jama.com. JAMA, Jan. 14, 2009, vol. 301, No. 2, pp. 175-182.
R.A. Gibson et al. "Effect of increasing breast milk docosahexaenoic acid on plasma and erythrocyte phospholipid fatty acids and neural indices of exclusively breast fed infants" European Journal of Clinical Nutrition (1997) vol. 51, pp. 578-584.
M. Makrides et al. "Effect of maternal docosahexaenoic acid (DHA) supplementation on breast milk composition" European Journal of Clinical Nutrition (1996) vol. 50, pp. 352-357.

(Continued)

Primary Examiner — Paul Zarek
(74) Attorney, Agent, or Firm — Morris, Manning & Martin, LLP; Christopher W. Raimund

(57) ABSTRACT

The present invention relates to methods for promoting the neurological development of an infant by administration of fatty acids and compositions comprising same, wherein the fatty acids are enriched with respect to docosahexaenoic acid (DHA) content.

45 Claims, No Drawings

(56) References Cited

OTHER PUBLICATIONS

Lisa G. Smithers et al. "Higher dose of docosahexaenoic acid in the neonatal period improves visual acuity of preterm infants: results of randomized controlled trial 1-4" Am. J. Clin. Nutr. (2008), vol. 88, pp. 1049-1056.
"Preterm Female Babies May Be Helped by Omega-3 Fatty Acid" TopNews, Arkansas—Jan. 14, 2009 (1 page).
"Study: DHA Supplements May Help Premature Baby Girls" USA Today, http://www.usatoday.com/news/health/2009-01-13-DHA-preemies_N.htm (2 pages) Jan. 13, 2009.
"Study: Fish Oil For Preemies May Boost Cognition" TIME, http://www.time.com/time/health/article/0,8599,1871514,00.html (3 pages) Jan. 13, 2009.
"DHA supplements aid neuro-development in preemie girls" TheMed Guru, India Jan. 14, 2009 (2 pages).
"Fish Oil Cuts Risk of Mental Delay In Early Babies" The Australian, Health Editor, Jan. 15, 2009 (2 pages).
"Omega-3 fatty acid is early boost for female preemies-DHA given to newborns in the first weeks following birth improves brain development in girls, but not boy" Magazine of the Society for Science & the Public, www.sciencenews.org, Web Edition, Jan. 13, 2009 (2 pages).
M. Makrides, et al. "Breakthrough made in premature baby care" Toowoomba Chronicle, Australia, Jan. 14, 2009 (2 pages).
M. Makrides, et al. "Intake of Certain Fatty Acid Appears to Improve Neurodevelopment for Preterm Girls, But Not Boys" Science Daily, Jan. 13, 2009 http://www.sciencedaily.com/releases/2009/01/090113174430.htm (2 pages).
M. Makrides, et al. "Breakthrough In Treating Premature Babies: Omega 3 Fatty Acid Supplement" Science Daily Jan. 14, 2009, http://www.sciencedaily.com/releases/2009/01/090114092844.htm (2 pages).
M. Makrides, et al. "DHA and Mental Health" Jan. 14, 2009 Natural Products Industry Insider, Arizona, http://www.naturalproductsinsider.com/.
M. Makrides, et al. "Only Some Preemies Get Mental Boost from Fatty Acid Supplement" MedPage Today, NJ, Jan. 13, 2009 (3 pages).
M. Makrides, et al. "Tuna Fish Oil Helps Premature Babies Develop Normally" www.mangalorean.com, India, Jan. 16, 2009 (1 page).
M. Makrides, et al. "Neurodevelopmental Outcomes of Preterm Infants Fed High-Dose Docosahexaenoic Acid" JAMA (subscription) IL, vol. 301, No. 2, Jan. 14, 2009 (2 pages).
M. Makrides, et al. "Omega-3 Fatty Acid Helps Preemies" Medical Breakthroughs, http://www.ivanhoe.com, Jan. 15, 2009 (2 pages).
"Omega-3 Fatty Acids Improve the Mental Development of Premature Baby Girls" eFluxMedia, Jan. 14, 2009 (1 page).
"Breakthrough Treatment for Premie Babies Developed" ChattahBox, MA, Jan. 14, 2009, http://chattahbox.com/health/2009/01/14/breakthrough-treatment-for-premie-babies-developed/ (1 page).
"Omega-3 Fatty Acid May Help 'Preemie' Girls' Brains" HealthDay Reporter, www.washingtonpost.com, Jan. 13, 2009 (2 pages).
"Adelaide Specialist's Development Boon For Premature Babies" The Advertiser, Jan. 15, 2009 (1 page).
"Breakthrough For Tiny Babies" The Canberra Times, Australia, Jan. 14, 2009, www.canberratimes.com.au.
"Oral Presentations" New Zealand, Hawaii, Missouri, Australia (1 page).
M. Makrides, et al. "Does High-dose dietary docosahexaenoic acid (DHA) improve the neurodevelopmental outcome of preterm infant born <33 weeks? The outcomes of the DINO Trial" (1 page), 2008.
M. Makrides, et al. "Does High-dose dietary docosahexaenoic acid (DHA) improve the neurodevelopmental outcome of preterm infants?" (1 page), 2008.
The DINO Trial Slide Show Lecture (4 pages), 2008.
M. Makrides, et al. "The DINO Trial outcomes: Does High-dose dietary Docosahexaenoic Acid (DHA) Improve the Neurodevelopmental Outcome of Preterm Infants?" (Abstract), 2008.
The DINO Trial Slide Show Lecture (8 pages), 2008.
M. Makrides, et al. "The DINO Trial outcomes: Does High dose dietary Docosahexaenoic Acid Improve the Neurodevelopmental Outcome of Preterm Infants?" (Abstract), 2008.
"Omega-3 to Benefit Premature Babies: SA Research" ABC Online, Australia, Jan. 14, 2009 (1 page).
"Trial from ANZCTR—The Dino Trial," Australia New Zealand Clinical Trials Registry, Trial registeredon Mar. 27, 2003 (online) URL: https://www.anzctr.org.au/Trial/Registration/TrialReview.aspx?id=1427&showOriginal=true.
J.A. Greenberg, et al., "Omega-3 Fatty Acid Supplementation During Pregnancy", Reviews in Obstetrics & Gynecology, 2008, 1(4): 162-169, MedReviews, LLC.
L.D.Arbuckle, et al., "Docosahexaenoic Acid Is Transferred through Maternal Diet to Milk and to Tissues of Natural Milk-Fed Piglets", The Journal of Nutrition, May 25, 1993, 123: 1668-1675, American Institute of Nutrition.
R. Chulei, et al., "Milk Composition in Women from Five Different Regions of China: The Great Diversity of Milk Fatty Acids", The Journal of Nutrition, Aug. 24, 1995, 125: 2993-2998, American Institute of Nutrition.
C.L. Jensen, et al., Effects of maternal docosahexaenoic acid intake on visual function and neurodevelopment in breastfed term infants, The American Journal of Clinical Nutrition, 2005, 82: 125-132, American Society for Clinical Nutrition, USA.
D.R. Hoffman, et al., Effects of supplementation with ω3 long-chain polyunsaturated fatty acids on retinal and cortical development in premature infants, The American Journal of Clinical Nutrition, 1993, 57(suppl): 807S-812S, American Society for clinical nutrition, USA.
Y.Yeh, et al., "Modification of Milk Formula to Enhance Accretion of Long-Chain n-6 and n-3 Polyunsaturated Fatty Acids in Artificially Reared Infant Rats", Lipids, May 1998, 33(5): 513-520, American Oil Chemists' Society.

\* cited by examiner

METHODS AND COMPOSITIONS FOR PROMOTING THE NEUROLOGICAL DEVELOPMENT OF AN INFANT

This application claims the benefit of U.S. Provisional Application No. 61/170,685, filed on Apr. 20, 2009, which is incorporated by reference herein in its entirety.

TECHNICAL FIELD

The present invention is directed to methods for promoting the neurological development of an infant by administration of fatty acids and compositions comprising same, wherein the fatty acids are enriched with respect to docosahexaenoic acid content.

BACKGROUND OF THE INVENTION

Preterm infants and in particular infants born prior to 33 weeks gestation are at an increased risk for developmental disorders and learning disabilities. Long-term outcome studies of preterm infants show an overall reduction in developmental quotient (DQ) and a poorer performance on tests of visual-motor integration, spatial relations, quantitative concepts and classroom behaviour compared with reference norms. Such studies suggest that preterm infants may face significant educational and developmental challenges during adolescence and also in later life. There is therefore a need for methods by which the risk of developmental disorders and learning disabilities in preterm infants can be minimised or even eliminated.

An inadequate nutrient supply in the neonatal period is hypothesized to contribute to the observed poor developmental outcome in preterm infants. The n-3 long chain polyunsaturated fatty acid, docosahexaenoic acid (DHA) is of particular interest in this regard because it is a major lipid in the brain with specific structural and functional roles in neurological development. The uptake of DHA into the developing brain is maximised during the final trimester of pregnancy and as a result preterm infants do not receive the DHA in utero that is received by their full term counterparts.

DHA is known to significantly alter a number of basic properties of cell membranes including permeability, fluidity and interactions with regulatory proteins. One such property includes a modulating effect on the activity of ion channels which may facilitate electrical signalling, cellular communication and possibly brain functions such as memory, processing and the ability to learn.

The present inventors have surprisingly discovered that the neurological development of an infant can be promoted by administration of an increased daily amount of DHA compared to that considered previously.

SUMMARY OF THE INVENTION

In a first aspect, the present invention provides a method for promoting the neurological development of an infant, the method comprising administration to the infant of DHA in an amount of at least about 30 mg/kg of body weight per day.

The DHA may be administered in an amount of at least about 60 mg/kg of body weight per day.

The DHA may be administered in an amount of at least about 90 mg/kg of body weight per day.

The infant may be a preterm infant.

The infant may be born prior to 33 weeks gestation, or prior to 36 weeks gestation.

The administration may be continued until the infant reaches term corrected age.

The infant may be classified as small for gestational age.

The infant may have a birth weight of less than or equal to about 1250 g.

The administration of DHA may commence within about 24 hours of the birth of the infant.

The administration of DHA may commence at a time when the infant commences enteral feeding.

The administration may be enteral or parenteral administration.

The DHA may be administered to the infant in combination with a source of protein.

The DHA may be administered to the infant in combination with vitamins and/or minerals.

The DHA may be administered to the infant in combination with one or more of the following: human milk, infant formula and human milk fortifier.

The DHA may be administered in the form of an emulsion.

The infant may be a female.

The infant may be in utero.

The administration of DHA may commence when the infant is in utero and continue after birth of the infant.

The infant's mother may have been identified as being at risk of giving birth to the infant preterm, or at risk of giving birth to an infant that will be classified as small for gestational age.

In a second aspect, the present invention provides a method for promoting the neurological development of an infant, the method comprising administration to the infant fatty acids including DHA, wherein the DHA represents about 1% or more of the fatty acids.

The DHA may be present in an amount of more than 1% of the fatty acids.

The DHA may present in an amount between more than 1% and about 30% of the fatty acids.

The infant may be a preterm infant.

The infant may be born prior to 33 weeks gestation, or prior to 36 weeks gestation.

The administration of DHA may be continued until the infant reaches term corrected age.

The infant may be classified as small for gestational age.

The infant may have a birth weight of less than or equal to about 1250 g.

The administration of DHA may commence within about 24 hours of the birth of the infant.

The administration of DHA may commence at a time when the infant commences enteral feeding.

The administration may be enteral or parenteral administration.

DHA may be administered to the infant at least once a day.

DHA may be administered to the infant at least three times a day.

DHA may be administered to the infant at least five times a day.

The DHA may be administered to the infant in combination with a source of protein.

The DHA may be administered to the infant in combination with vitamins and/or minerals.

The DHA may be administered to the infant in combination with one or more of the following: human milk, infant formula and human milk fortifier.

The DHA may be administered in the form of an emulsion.

The infant may be a female.

The infant may be in utero.

The administration of DHA may commence when the infant is in utero and continues after birth of the infant.

The infant's mother may been identified as being at risk of giving birth to the infant preterm, or at risk of giving birth to an infant that will be classified as small for gestational age.

In a third aspect, the present invention provides a method of feeding an infant, the method comprising:
  (i) administering fatty acids including DHA to the infant's mother in an amount sufficient to provide a content of DHA in the breast milk of the infant's mother that is about 1% or more of the total fatty acids present in the breast milk, and
  (ii) feeding the infant with breast milk following step (i).

Step (i) may comprise administering fatty acids including DHA to the infant's mother in an amount and over a time period sufficient to provide a constant DHA content in the breast milk of the infant's mother that is about 1% or more of the total fatty acids present in the breast milk of the infant's mother.

Step (i) may comprise administering fatty acids including DHA to the infant's mother on a daily basis, and wherein the daily dosage of DHA is greater than about 600 mg.

Step (i) may comprise administering fatty acids including DHA to the infant's mother on a daily basis, and wherein the daily dosage of DHA is greater than about 800 mg.

Step (i) may comprise administering fatty acids including DHA to the infant's mother on a daily basis, and wherein the daily dosage of DHA is about 900 mg or greater.

The infant may be a pre-term infant.

The infant may be born prior to 33 weeks gestation, or prior to 36 weeks gestation.

The feeding may be continued until the infant reaches term corrected age.

The infant may be classified as small for gestational age.

The infant may have a birth weight of less than or equal to about 1250 g.

The feeding may commence within about 24 hours of the birth of the infant.

Step (ii) may be commenced about 1 week after commencement of step (i).

The feeding may be carried out at least once a day.

The feeding may be carried out at least three times a day.

The feeding may be carried out at least five times a day.

The infant may be a female.

In a fourth aspect, the present invention provides an infant formula comprising fatty acids including DHA, wherein the DHA is present in an amount of about 1% or more of the total fatty acid content in the formula.

The formula may be specialised preterm infant formula.

In a fifth aspect, the present invention provides a composition comprising fatty acids including DHA, wherein the DHA is present in an amount of about 1% or more of the total fatty acid content in the composition.

The composition may be a unit dosage form.

The composition may be adapted for parenteral administration.

The composition may further comprise one or more carriers, diluents and/or adjuvants.

DEFINITIONS

In the context of the present specification, the terms "a" and "an" are used herein to refer to one or to more than one (i.e. to at least one) of the grammatical object of the article. By way of example, "an element" means one element or more than one element.

In the context of the present specification, the term "comprising" means "including principally but not necessarily solely". Furthermore, variations of the word "comprising", such as "comprise" and "comprises", have correspondingly varied meanings.

In the context of this specification, the term "about" is understood to refer to a range of numbers that a person of skill in the art would consider equivalent to the recited value in the context of achieving the same function or result.

In the context of this specification reference to "x % of the total fatty acid content of the composition" or "x % of the total fatty acid content of the formula" or "x % of the total fatty acid content of the mixture" and the like means x % by weight of the total fatty acid content of the composition, formula or mixture.

In the context of this specification, the term "neurological development" generally refers to growth of the brain and neurological system and to the ability of the infant to assimilate and process information. Neurological development may be assessed by any suitable means and/or criteria. Assessment may be biochemical, psychological and/or behavioural. One suitable means of assessing neurological development is the Bayley Mental Development Index (MDI).

In the context of this specification, the term "infant" means a being that is less than 24 months of age, and is not limited to a human. The term "infant" is therefore to be construed as encompassing animals, and in particular mammals, including placental mammals, monotremes and marsupials.

In the context of this specification, the term "preterm infant" as it relates to a human being means an infant that is born prior to 37 weeks gestation.

In the context of this specification, the term "preterm infant" as it relates to a non-human being means an infant that is born after the period of viability, but before full term.

In the context of this specification, the term "small for gestational age" means an infant whose birth weight lies below the tenth percentile for that gestational age.

In the context of the present specification, the term "term corrected age" as it relates to a preterm human being means an age corresponding to between 37 and 40 weeks gestation had the being achieved full term. For example, if a human being is born at 30 weeks gestation, then the "term corrected age" will be reached between 7 and 10 weeks after birth.

In the context of the present specification, the term "specialised preterm infant formula" means an infant formula intended for administration to preterm infants only comprising selected ingredients so as to satisfy the unique nutritional requirements of preterm infants.

In the context of this specification, the terms "infant formula" and "infant formulas" include formulas that are intended as breast milk replacements or supplements and also milk fortifiers.

DETAILED DESCRIPTION OF THE INVENTION

As exemplified herein, the administration of DHA and fatty acids as described in accordance with the present invention has been shown to have a positive effect on a number of indicators of neurological development as assessed by the Bayley Mental Development Index. Accordingly, particular embodiments of the invention relate to methods of promoting neurological development. In addition, as also exemplified herein the administration of DHA and fatty acids as described is shown to reduce a number of clinical manifestations of allergy, including hayfever. Thus, methods of the invention also find application in the treatment or prevention of allergic conditions such as hayfever.

In a first aspect, the present invention relates to a method for promoting the neurological development of an infant, the method comprising administration to the infant of DHA in an amount of at least about 30 mg/kg of body weight per day.

In a second aspect, the present invention relates to a method for promoting the neurological development of an infant, the method comprising administration to the infant fatty acids including DHA, wherein the DHA represents about 1% or more of the fatty acids.

The methods of the invention promote neurological development in infants. A promotion of neurological development may be manifest by improvements in one or more measures of neurological development such as memory, learning and language and/or reductions in developmental delays and learning disabilities. Those skilled in the art will also appreciate that promoting neurological development may comprise preventing or treating neurological or developmental disorders or conditions, for example seizures and mental retardation.

In one embodiment, the method of the first aspect may comprise administration to the infant of DHA in an amount of at least 30 mg/kg of body weight per day, at least 32 mg/kg of body weight per day, at least 34 mg/kg of body weight per day, at least 36 mg/kg of body weight per day, at least 38 mg/kg of body weight per day, at least 40 mg/kg of body weight per day, at least 42 mg/kg of body weight per day, at least 44 mg/kg of body weight per day, at least 46 mg/kg of body weight per day, at least 48 mg/kg of body weight per day, at least 50 mg/kg of body weight per day, at least 52 mg/kg of body weight per day, at least 54 mg/kg of body weight per day, at least 56 mg/kg of body weight per day, at least 58 mg/kg of body weight per day, at least 60 mg/kg of body weight per day, at least 62 mg/kg of body weight per day, at least 64 mg/kg of body weight per day, at least 66 mg/kg of body weight per day, at least 68 mg/kg of body weight per day, at least 70 mg/kg of body weight per day, at least 72 mg/kg of body weight per day, at least 74 mg/kg of body weight per day, at least 76 mg/kg of body weight per day, at least 78 mg/kg of body weight per day, at least 80 mg/kg of body weight per day, at least 82 mg/kg of body weight per day, at least 84 mg/kg of body weight per day, at least 86 mg/kg of body weight per day, at least 88 mg/kg of body weight per day, at least 90 mg/kg of body weight per day, at least 92 mg/kg of body weight per day, at least 94 mg/kg of body weight per day, at least 96 mg/kg of body weight per day, at least 98 mg/kg of body weight per day, at least 100 mg/kg of body weight per day, at least 102 mg/kg of body weight per day, at least 104 mg/kg of body weight per day, at least 106 mg/kg of body weight per day, at least 108 mg/kg of body weight per day, or at least 110 mg/kg of body weight per day.

In another embodiment, the method of the first aspect may comprise administration to the infant of DHA in an amount between about 30 mg/kg of body weight per day and about 500 mg/kg of body weight per day, or between about 32 mg/kg of body weight per day and about 500 mg/kg of body weight per day, or between about 34 mg/kg of body weight per day and about 500 mg/kg of body weight per day, or between about 36 mg/kg of body weight per day and about 500 mg/kg of body weight per day, or between about 38 mg/kg of body weight per day and about 500 mg/kg of body weight per day, or between about 40 mg/kg of body weight per day and about 500 mg/kg of body weight per day, or between about 42 mg/kg of body weight per day and about 500 mg/kg of body weight per day, or between about 44 mg/kg of body weight per day and about 500 mg/kg of body weight per day, or between about 46 mg/kg of body weight per day and about 500 mg/kg of body weight per day, or between about 48 mg/kg of body weight per day and about 500 mg/kg of body weight per day, or between about 50 mg/kg of body weight per day and about 500 mg/kg of body weight per day, or between about 52 mg/kg of body weight per day and about 500 mg/kg of body weight per day, or between about 54 mg/kg of body weight per day and about 500 mg/kg of body weight per day, or between about 56 mg/kg of body weight per day and about 500 mg/kg of body weight per day, or between about 58 mg/kg of body weight per day and about 500 mg/kg of body weight per day, or between about 60 mg/kg of body weight per day and about 500 mg/kg of body weight per day, or between about 62 mg/kg of body weight per day and about 500 mg/kg of body weight per day, or between about 64 mg/kg of body weight per day and about 500 mg/kg of body weight per day, or between about 66 mg/kg of body weight per day and about 500 mg/kg of body weight per day, or between about 68 mg/kg of body weight per day and about 500 mg/kg of body weight per day, or between about 70 mg/kg of body weight per day and about 500 mg/kg of body weight per day, or between about 72 mg/kg of body weight per day and about 500 mg/kg of body weight per day, or between about 74 mg/kg of body weight per day and about 500 mg/kg of body weight per day, or between about 76 mg/kg of body weight per day and about 500 mg/kg of body weight per day, or between about 78 mg/kg of body weight per day and about 500 mg/kg of body weight per day, or between about 80 mg/kg of body weight per day and about 500 mg/kg of body weight per day, or between about 82 mg/kg of body weight per day and about 500 mg/kg of body weight per day, or between about 84 mg/kg of body weight per day and about 500 mg/kg of body weight per day, or between about 86 mg/kg of body weight per day and about 500 mg/kg of body weight per day, or between about 88 mg/kg of body weight per day and about 500 mg/kg of body weight per day, or between about 90 mg/kg of body weight per day and about 500 mg/kg of body weight per day, or between about 92 mg/kg of body weight per day and about 500 mg/kg of body weight per day, or between about 94 mg/kg of body weight per day and about 500 mg/kg of body weight per day, or between about 96 mg/kg of body weight per day and about 500 mg/kg of body weight per day, or between about 98 mg/kg of body weight per day and about 500 mg/kg of body weight per day, or between about 100 mg/kg of body weight per day and about 500 mg/kg of body weight per day, or between about 30 mg/kg of body weight per day and about 300 mg/kg of body weight per day, or between about 35 mg/kg of body weight per day and about 300 mg/kg of body weight per day, or between about 40 mg/kg of body weight per day and about 300 mg/kg of body weight per day, or between about 45 mg/kg of body weight per day and about 300 mg/kg of body weight per day, or between about 50 mg/kg of body weight per day and about 300 mg/kg of body weight per day, or between about 55 mg/kg of body weight per day and about 300 mg/kg of body weight per day, or between about 60 mg/kg of body weight per day and about 300 mg/kg of body weight per day, or between about 65 mg/kg of body weight per day and about 300 mg/kg of body weight per day, or between about 70 mg/kg of body weight per day and about 300 mg/kg of body weight per day, or between about 75 mg/kg of body weight per day and about 300 mg/kg of body weight per day, or between about 80 mg/kg of body weight per day and about 300 mg/kg of body weight per day, or between about 85 mg/kg of body weight per day and about 300 mg/kg of body weight per day, or between about 90 mg/kg of body weight per day and about 300 mg/kg of body weight per day, or between about 95 mg/kg of body weight per day and about 300 mg/kg of body weight per day, or between about 100 mg/kg of body weight per day and about 300 mg/kg of body weight per day, or between about 30 mg/kg of body weight per day and about 200 mg/kg of body weight per day, or between about 40 mg/kg of body weight per day and about 200 mg/kg of body weight per day, or between about 50 mg/kg of body weight per day and about 200 mg/kg of body weight per day, or between about 60 mg/kg of body weight per day and about 200 mg/kg of body weight per day, or between about 70 mg/kg of body weight per day and about 200 mg/kg of body weight per day, or between about 80 mg/kg of body weight per day and about 200 mg/kg of body weight per day, or between about 90 mg/kg of body weight per day and about 200 mg/kg of body weight per day, between about 60 mg/kg of body weight per day and about 180 mg/kg of body weight per day, between about 60 mg/kg of body weight per day and about 150 mg/kg of body weight per day, or between about 60 mg/kg of body weight per day and about 120 mg/kg of body weight per day.

In another embodiment, the method of the first aspect may comprise administration to the infant of DHA in an amount of about 30, 40, 50, 60, 70, 80, 90, 100, 110, 120, 130, 140, 150, 160, 170, 180, 190, 200, 210, 220, 230, 240, 250, 260, 270, 280, 290 or 300 mg/kg of body weight per day.

In the method of the second aspect, the DHA may represent about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more of the fatty acids.

In the method of the second aspect, the DHA may represent between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the fatty acids.

The infant may be a preterm infant. In an alternative embodiment the infant may be an infant classified as small for gestational age. Infants that are classified as small for gestational age are typically growth restricted in utero and hence may not have received an adequate supply of DHA. Such infants may therefore derive significant benefit from the methods of the present invention.

The preterm infant may be born prior to 37 weeks gestation, or prior to 36 weeks gestation, or prior to 35 weeks gestation, or prior to 34 weeks gestation, or prior to 33 weeks gestation, or prior to 32 weeks gestation, or prior to 31 weeks gestation, or prior to 30 weeks gestation, or prior to 29 weeks gestation, or prior to 28 weeks gestation, or prior to 27 weeks gestation, or prior to 26 weeks gestation, or prior to 25 weeks gestation, or prior to 24 weeks gestation, or prior to 23 weeks gestation.

The methods and compositions described herein find particular application in relation to infant mammals, for example infant humans. However those skilled in the art will appreciate that the scope of the invention is not so limited and that the compositions and formulas described herein may be administered to infants of any species for the purposes of nutrition and promoting neurological development, such as in laboratory animals, domestic pets, livestock, the young of stud animals and in rare or endangered species, for example as part of conservation measures in zoological parks and gardens.

The DHA may be administered to the infant via an enteral route or a parenteral route depending on the chronological age of the infant, general health of the infant and whether the infant has commenced enteral feeding. Where the infant has not yet commenced enteral feeding the DHA may be administered parenterally, for example intravenously. Where the infant has commenced enteral feeding the DHA may be administered enterally, for example orally. The method of enteral administration selected will often depend on chronological age, birth weight and the clinical condition of the infant. Typically the route of enteral administration is determined by the infant's ability to co-ordinate sucking, swallowing and breathing. Infants who are less mature, weak or suffering from an illness may require enteral administration via tube or possibly nasogastrically or orogastrically.

Administration of DHA may commence as soon as possible after the birth of the infant. For example, administration may commence within about 24 hours of the birth of the infant, or within about 12 hours of the birth of the infant, or within about 10 hours of the birth of the infant, or within about 8 hours of the birth of the infant, or within about 6 hours of the birth of the infant, or within about 5 hours of the birth of the infant, or within about 4 hours of the birth of the infant, or within about 3 hours of the birth of the infant, or within about 2 hours of the birth of the infant, or within about 1 hour of the birth of the infant.

In another embodiment, administration to the infant may commence at a time when the infant commences enteral feeding. For example, DHA may be administered within about 24 hours, or within about 12 hours, or within about 8 hours, or within about 4 hours, or within about 2 hours of the infant commencing enteral feeding. In an alternative embodiment administration of DHA may commence simultaneously when the infant commences enteral feeding.

In a further embodiment, administration may begin while the infant is still in utero. For example, the infant's mother may be identified as being at risk of delivering the infant preterm (risk factors may include smoking), or the infant's mother may have been scheduled to give birth by caesarean section. Alternatively or in addition, the infant whilst in utero may be identified as being likely to be classified as small for gestational age at birth. In such circumstances it may be desirable to begin administration of fatty acids in accordance with methods of the invention prior to birth of the infant. Such administration will then typically continue beyond birth, as described herein.

The commencement of DHA administration may be determined on a case-by-case basis and could depend on a number of factors including for example the number of weeks gestation and the general health of the infant post birth.

Where the infant is a preterm infant administration may continue until the infant reaches term corrected age. For example, if the infant is born at 32 weeks gestation administration of DHA may be continued until the infant reaches what would have been full term, i.e. between 37 and 40 weeks gestation, or in other words until the infant reaches a chronological age of between 5 and 8 weeks. Alternatively, if desired, termination of administration may occur at anytime prior to the infant reaching term corrected age.

In alternative embodiments DHA may be administered prior to and beyond term corrected age, for example prior to, and up to 24 months after, term corrected age; or prior to, and up to 18 months after, term corrected age; or prior to, and up to 12 months after, term corrected age; or prior to, and up to 6 months after, term corrected age.

Where the infant is a full term infant and classified as small for gestational age, administration may also commence at a time when the infant commences enteral feeding and may continue for up to 24 months after birth, or up to 18 months after birth, or up to 12 months after birth, or up to 9 months after birth, or up to 6 months after birth, or up to 3 months after birth.

Fatty acids administered in accordance with methods described herein may be administered as part of a composition. Such compositions may take a number of forms that are well known to those skilled in the art including tablets, capsules, caplets, powders, solutions, suspensions and emulsions. The form of the composition is not critical to the invention as long as the infant receives the required amount of DHA. The form of the composition will depend on the intended route of administration. Those skilled in the art will readily appreciate that a number of suitable processes and techniques exist for the manufacture of compositions suitable for enteral and parenteral administration and that the invention is not limited by reference to any one particular process or technique. The methods may involve administration of the composition to the infant once, twice, three, four, five, six or more times per day.

The compositions may be administered to the infant in combination with a source of protein. Protein sources are well known to those skilled in the art and include milk, whey protein, casein, vegetable protein, animal protein, cereal protein, hydrolysed protein, amino acids, peptides and the like. In the case of humans, the source of protein may be human milk, infant formula, human milk fortifier or combinations thereof. The composition may also be administered to an infant in combination with various vitamins and/or minerals which are commonly given to preterm infants and infants classified as small for gestational age. Examples of such vitamins and minerals include, but are not limited to: vitamin A, B group vitamins (for example vitamins $B_1$, $B_2$, $B_5$, $B_6$, $B_9$ and $B_{12}$), vitamin C, vitamin D, vitamin E, vitamin K, vitamin H, zinc, selenium, calcium, phosphorus, sodium, potassium, chloride, manganese, phosphorus, iodine, copper, iron, magnesium, molybdenum and chromium.

In the methods of the invention the DHA may be administered as part of an infant formula. The compositions used in the method of the second aspect may be commercially available infant formulas (for example formulas intended for administration to preterm infants) that have been supplemented such that DHA is present in an amount of about 1% or more of the total fatty acid content of the formula (presently available infant formulas typically comprise DHA in an amount of about 0.3% of the total fatty acid content). The DHA supplementation may occur during manufacture of the formula or alternatively post manufacture. DHA supplementation during manufacture may be performed by replacing the usual fatty acid source or sources with an alternative fatty acid source having the desired DHA content as a percentage of total fatty acids. Alternatively, purified DHA may simply be added to the formula either during or after manufacture so as to achieve the desired DHA content as a percentage of total fatty acids.

The method of the second aspect may involve administering the DHA-supplemented formula according to the daily dosage regime specified by the manufacturer of the formula so that the infant conveniently receives the specified amount of DHA as a percentage of total fatty acid content at each feed. Suitable infant formulas that may be supplemented and administered in this manner include but are not limited to: S-26 LBW Gold available from Wyeth Nutrition, Baulkham Hills, NSW Australia, Nutriprem available from Nutricia, Macquarie Park, NSW Australia, preterm formulas sold under the trade name Enfamil® by MeadJohnson, Indiana, USA, and preNAN® available from Nestle Australia Ltd, Rhodes, NSW Australia.

In an alternative embodiment, the method of the second aspect may involve the use of a DHA-supplemented commercial human milk fortifier which may be intended for administration to preterm infants and which comprises an amount of DHA such that when the fortifier is admixed with an appropriate amount of breast milk, the amount of DHA in the resulting mixture is about 1% or more of the total fatty acid content of the mixture. Typically the amount of DHA added to the human milk fortifier would be calculated on the assumption that mothers consume a minimal amount of DHA-containing products so as to ensure that when the human milk fortifier is added to different breast milks having a range of different DHA contents, the amount of DHA in the resultant mixtures will always be about 1% or more of the total fatty acid content of the mixture. For example, the average amount of DHA as a percentage of total fatty acids in the milk of mothers consuming a typical western diet is less than 0.3%. Accordingly, the amount of DHA present in the DHA-supplemented commercial human milk fortifier would be an amount sufficient to increase this percentage to about 1% or more when admixed with an appropriate amount of breast milk. Suitable commercial human milk fortifiers that may be supplemented and administered in the manner described include but are not limited to: products sold under the trade name Similac® by Abbott Nutrition, Illinois USA, fortifiers sold under the trade name Enfamil® by MeadJohnson, Indiana, USA, S-26 HMF available from Wyeth Nutrition, Baulkham Hills, NSW Australia, and FM-85 available from Nestle Australia Ltd, Rhodes, NSW Australia.

The method of the first aspect may involve administration to the infant of purified DHA, DHA that is present as part of a mixture of fatty acids or any composition comprising DHA (for example infant formulas and human milk fortifiers), so long as the daily dosage of DHA received by the infant is within the dosage regimes described herein.

The source of DHA in the methods, compositions and formulas described herein may be any source known in the art, including plant and marine sources. The plant and marine sources may be genetically modified or non-genetically modified. Marine sources include, but are not limited to: crustaceans such as krill, molluscs such as oysters, and fish such as salmon, trout, sardines, tuna, mackerel, sea bass, menhaden, herring, pilchards, kipper, eel or whitebait. The DHA may be present in a purified form and/or in the form of an extract from a suitable source. The DHA may be present as a component of fish oil. The fish oil may be obtained from, for example one or more of the following fish: tuna, salmon, trout, menhaden, sea bass, mackerel, sardines, pilchards, herring, kipper, eel, whitebait or any other "fatty fish".

The DHA may be stabilised so as to protect against oxidation and other forms of degradation. The stabilisation may be achieved by encapsulation. Suitable encapsulation methods include, but are not limited to: coatings (including primary, secondary and tertiary), emulsions, coacervasion and gels. The DHA may alternatively be stabilised in the form of an emulsion wherein the DHA is either not, or only partially encapsulated.

Preterm human infants and human infants classified as small for gestational age are typically able to consume milk and/or formula in an amount between about 100 mL and 250 mL per kg of body weight per day. Accordingly, the method of the second aspect may comprise administration to the infant of milk and/or formula in an amount between about 100 mL and 250 mL per kg of body weight per day, wherein the DHA content of the milk or formula is about 1% or more of the total fatty acid content of the milk or formula. The milk and/or formula may be administered to the infant once a day or on multiple occasions depending on the infant's age, general health and feeding regime. As the infant grows, the amount of milk and/or formula can be increased in accordance with the infant's nutritional requirements.

In a third aspect, the present invention relates to a method of feeding an infant, the method comprising:
 (i) administering fatty acids including DHA to the infant's mother in an amount sufficient to provide a content of DHA in the breast milk of the infant's mother that is about 1% or more of the total fatty acids present in the breast milk, and
 (ii) feeding the infant with breast milk following step (i).

The infant may be a preterm infant or an infant classified as small for gestational age. The feeding may comprise breast feeding or alternatively bottle feeding using expressed milk from the breast of the infant's mother.

Step (i) may comprise administering fatty acids including DHA to the infant's mother in an amount sufficient to provide a content of DHA in the breast milk of the infant's mother that is at least 1%, or at least 1.05%, or at least 1.1%, or at least 1.2%, or at least 1.3%, or at least 1.4%, or at least 1.5%, or at least 1.6%, or at least 1.7%, or at least 1.8%, or at least 1.9%, or at least 2%, or at least 2.1%, or at least 2.2%, or at least 2.3%, or at least 2.4%, or at least 2.5%, or at least 2.6%, or at least 2.7%, or at least 2.8%, or at least 2.9%, or at least 3.0% of the total fatty acids present in the breast milk.

Step (i) may comprise administering fatty acids including DHA to the infant's mother in an amount sufficient to provide a content of DHA in the breast milk of the infant's mother that is between more than 1% and about 20%, or between more than 1.05% and about 20%, or between more than 1.1% and about 20%, or between more than 1% and about 30%, or between more than 1% and about 25%, or between more than 1% and about 15%, or between more than 1% and about 10%, or between about 1.5% and about 20%, or between about 1.5% and about 15%, or between about 1.5% and about 10%, or between about 1.5% and about 5%, or between about 2% and about 20%, or between about 2% and about 15%, or between about 2% and about 10%, of the total fatty acids present in the breast milk.

Step (i) may comprise administering fatty acids including DHA to the infant's mother in an amount and over a time period sufficient to provide a constant DHA content in the breast milk of the infant's mother that is about 1% or more of the total fatty acids present in the breast milk of the infant's mother. This outcome may be achieved by administering to the infant's mother approximately 600 mg or more of DHA per day. However, in the case of a mother who consumes minimal DHA as part of her diet, the amount of DHA administered on a daily basis may be approximately 900 mg or more. In the case of a mother who consumes a diet rich in DHA, it may be possible to achieve a content of DHA in the breast milk of the infant's mother that is about 1% or more of the total fatty acids present by administering less than 600 mg of DHA per day. Those skilled in the art will be capable of determining the amount of DHA required to be administered to an infant's mother in order to achieve a desired amount of DHA as a percentage of total fatty acids in breast milk by routine trial and experimentation based on the teachings herein.

In one embodiment, the amount of DHA administered to the infant's mother may be between about 600 mg per day and about 4000 mg per day, or between about 600 mg per day and about 3500 mg per day, or between about 600 mg per day and about 3000 mg per day, or between about 600 mg per day and about 2500 mg per day, or between about 600 mg per day and about 2000 mg per day, or between about 600 mg per day and about 1500 mg per day, or between about 600 mg per day and about 1200 mg per day.

The DHA may be administered in multiple unit dosage forms (such as tablets or capsules for example), or alternatively in a single unit dosage form comprising the daily amount of DHA. The DHA may be administered in the form of DHA-rich tuna oil, for example the product sold under the trade name HiDHA® available from Nu-Mega Ingredients, Nathan, Queensland Australia. In manipulating the amount of DHA present in the breast milk, the naturally occurring amount of arachadonic acid present (about 0.4% to 0.6%) may not be substantially altered.

Step (ii) may be commenced at any time after step (i). In one embodiment step (ii) commences about 1 week after commencement of step (i) thereby ensuring that the desired amount of DHA in the breast milk has been reached and is essentially constant. Practically however it is likely that the infant's mother will simply commence step (i) whilst continuing the infant's standard feeding regime. Accordingly, the level of DHA in the breast milk being received by the infant will increase and subsequently be maintained at, or above, the desired level.

The method of the third aspect may commence at anytime after the birth of the infant, and in one embodiment within about 24 hours of the birth of the infant. Commencement of the method will of course be dependent on whether the infant is capable of breastfeeding or bottle feeding expressed milk. Where the infant is unable to commence breastfeeding or bottle feeding soon after birth, the method may be commenced once the infant is able to breastfeed or bottle feed successfully.

In a fourth aspect, the present invention relates to infant formulas comprising fatty acids including DHA, wherein the DHA is present in an amount of about 1% or more of the total fatty acid content in the formulas. The infant formulas may be milk fortifiers or formulas intended for use as breast milk replacements or supplements.

The DHA may be present in the formulas in an amount of about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more, of the total fatty acid content of the formulas.

In alternative embodiments, the DHA may be present in the formulas in an amount between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the total fatty acid content of the formulas.

The infant formulas in accordance with the invention will typically be nutritionally complete and include standard ingredients that are present in commercially available infant formulas and milk fortifiers, such as fat, protein, carbohydrate, vitamins and minerals. The nutritional composition of the formulas and fortifiers may be adjusted depending on the intended age group to which the formulas and fortifiers are to be administered. For example, in one embodiment the infant formulas are specialised preterm infant formulas and hence include selected ingredients so as to satisfy the unique nutritional requirements of preterm infants. Alternatively, where the formulas and fortifiers are intended to be administered to infants that are older than term corrected age, the nutritional composition may be adjusted to meet the differing nutritional requirements of such infants. The formulas may be in the form of liquids, powders or tablets and may be manufactured according to techniques well known to those skilled in the art.

In one embodiment, the infant formulas of the invention may be prepared by supplementing commercially available infant formulas or fortifiers with the desired amount of DHA as described above in connection with the second aspect. Suitable infant formulas that may be supplemented in this manner include, but are not limited to: products sold under the trade name Similac® by Abbott Nutrition, Illinois USA, products sold under the trade name S-26 (for example S-26 LBW Gold and S-26 HMF) available from Wyeth Nutrition, Baulkham Hills, NSW Australia, Nutriprem available from Nutricia, Macquarie Park, NSW Australia, products sold under the trade name Enfamil® by MeadJohnson, Indiana, USA and FM-85 and preNAN®, both available from Nestle Australia Ltd, Rhodes, NSW Australia.

In a fifth aspect, the present invention relates to a composition comprising fatty acids including DHA, wherein the DHA is present in an amount of about 1% or more of the total fatty acid content in the composition.

The DHA may be present in the composition in an amount of about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more, of the total fatty acid content of the composition.

In alternative embodiments, the DHA may be present in the composition in an amount between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the total fatty acid content of the composition.

The composition may comprise one or more acceptable carriers, diluents and/or adjuvants. The carriers, diluents and adjuvants must be "acceptable" in terms of being compatible with the other components of the composition and not deleterious to the recipient thereof.

Suitable carriers, diluents and adjuvants will depend on the intended route of administration and are well known to those skilled in the art. In one embodiment, the composition may be adapted for parenteral administration. For administration as an injectable solution or suspension non-toxic parenterally acceptable diluents or carriers can include: Ringer's solution, isotonic saline, glucose solution, distilled water and phosphate buffered saline. Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may be a unit dosage form suitable for oral administration, for example a tablet, capsule, caplet, or lozenge. Unit dosage forms may optionally include one or more acceptable excipients, for example ethyl cellulose, cellulose acetate phthalates, mannitol, lactose, starch, magnesium stearate, sodium saccharin, talc, glucose, sucrose, carbonate, and the like.

The invention will now be described in more detail, by way of illustration only, with respect to the following examples. The examples are intended to serve to illustrate this invention and should not be construed as limiting the generality of the disclosure of the description throughout this specification.

EXAMPLE

Clinical study

Study Design and Methodology

A multi-centre randomized controlled trial was conducted in 5 Australian perinatal centres. Ethics approval was granted by the local Institutional Review Boards (Human Research Ethics Committees) of each centre. The trial began with a pilot phase at the Women's and Children's Hospital, Adelaide. A central trial coordinator monitored data collection, entry and checking An independent serious adverse event committee reviewed all deaths.

Infants born <33 weeks were eligible and families were approached by the research nurses within 5 days of their infant receiving any enteral feeds. Infants were excluded if they had major congenital or chromosomal abnormalities, were from a multiple birth where not all live born infants were eligible, or were in other trials of fatty acid supplementation. Lactating mothers in whom tuna oil was contraindicated, for example bleeding disorders or therapy with anticoagulants, were also excluded.

Once written informed consent was obtained, mother-infant pairs were randomly assigned a unique study number through a computer driven telephone randomization service according to an independently generated randomization schedule. Stratification was by centre, birth weight (<1250 g and ≤1250 g) and infant sex. Multiple births were considered a single randomization unit and randomization of twins or triplets was according to the sex and birth weight of the first born infant. Baseline characteristics, including maternal age, infant race as identified by parents, parental education, birth order, parity, gestational age at birth, birth measurements, pregnancy and birth complications, were recorded.

Lactating mothers allocated to the high-DHA group were asked to consume 6×500 mg DHA-rich tuna oil capsules per day in order to achieve a breast milk DHA concentration that was ≈1% of total fatty acids without altering the naturally occurring concentration of arachidonic acid (AA) in breast milk. If supplementary formula was required, infants were given a high-DHA preterm formula (≈1.0% DHA, 0.6% AA). Mothers with infants allocated to the standard DHA group were asked to consume 6×500 mg placebo, soy oil capsules that did not change the fat content or fatty acid composition of their milk. In the event that mothers chose not to breastfeed or could not produce enough breast milk, infants were fed standard preterm infant formula (≈0.35% DHA and 0.6% AA). To facilitate blinding, each treatment group was separately colour coded into two groups. All capsules were similar in size, shape and colour and were donated by Clover Corporation, Sydney, Australia. If formula was required in the pilot phase, two drops of oil from capsules in matching colour coded containers were added to each 90 mL jar of formula. For the remainder of the trial, Mead Johnson Nutritionals, IN, USA, specifically manufactured ready-to-feed preterm formula to trial specifications and packaged the formula according to the colour codes. The intervention continued until infants reached their expected date of delivery (EDD). Infants in the high-DHA group consumed approximately 60 mg/kg of body weight per day of DHA, whereas infants in the standard DHA group consumed approximately 20 mg/kg of body weight per day of DHA. Whilst in hospital, the feeding regimen was under the direction of the infant's clinician and did not interfere with the use of human milk fortifier or supplementary vitamins or minerals. Post-term, breastfeeding mothers were encouraged to continue breastfeeding and those who had weaned to formula were encouraged to use a term formula supplemented with DHA and AA. Parents were reimbursed the difference in cost between unsupplemented term formula and DHA-supplemented term formula.

During the intervention the proportion of parenteral and enteral nutrition, human milk and infant formula intakes, and the frequency of interrupted feeds were documented weekly. Confirmed cases of necrotizing enterocolitis (NEC), sepsis, intra-ventricular hemorrhage (IVH), retinopathy of prematurity (ROP) and oxygen treatment at 36 weeks were also documented. Weight, length and head circumference were assessed at EDD and women who were breastfeeding donated a 5 mL sample of milk to assess the fatty acid composition.[1] At EDD, women were also asked to guess their group allocation.

The Mental Development Index (MDI) of the Bayley Scales of Infant Development, Second Edition (BSID-II)[2] evaluates memory, habituation, problem solving, early number concepts and language. MDI at 18 months' corrected age was chosen as the primary outcome because it represents a robust assessment of mental delays in children, is reasonably correlated with IQ in preterm children[3] and allows comparison with other relevant studies. The psychomotor development index (PDI), which evaluates control of the gross muscle groups including movements associated with standing, walking, running and jumping, as well as fine motor manipulations involved in prehension, adaptive use of writing implements, and imitation of hand movements, was a secondary outcome. MDI and PDI scores standardized to a mean of 100 with a standard deviation of 15 (range from 50 to 150). If a child performed below the threshold of the tests for either MDI or PDI, they were assigned a score of 45. If they were completely untestable because of severe delay, they were assigned a score of 40. At the time of the BSID assessment weight, length and head circumference were measured and the Home Screening Questionnaire (HSQ)[4] was administered to assess the quality and quantity of cognitive, social and emotional support available to each infant in the home environment. Parents, clinicians and all research personnel were blinded to participant study group.

The trial was designed to evaluate the effect of high dietary DHA in the preterm period on infants born <33 weeks gestation as well as important subgroups in this heterogeneous population. We also planned a priori to conduct a sub-group analysis based on infant sex because DQ in early childhood often varies according to sex and differences of the order of 5-8 points have been reported. Overall, our recruitment target was 320 infants per group to allow for 10% loss to follow-up, including deaths.

All analyses were conducted according to the intention to treat principle. The a priori level of significance was $p<0.05$. Most of the outcomes were analysed using Generalized Estimating Equations (GEE)[5] to account for the clustering of infants within mother using SAS version 9.1 (SAS Institute Inc., Cary, N.C., USA). Normally distributed outcomes were analysed using a linear GEE, with the difference in means (95% CI) as the treatment effect. The subgroup analyses were performed via factorial models to allow testing for an interaction between treatment and subgroup. Outcomes that were counts were analysed using Poisson or Negative-Binomial GEE as appropriate, with the ratio of means (95% CI) as the treatment effect. Binary or categorical data were analysed using log-binomial GEE, with the relative risk (ratio of proportions) (95% CI) as the treatment effect. In secondary analyses the Bayley outcomes were also adjusted for the potential confounders of maternal education, infant sex, gestational age at delivery and birth order. An additional adjustment was made for phase of the study, which made little difference to the results. All other outcomes were adjusted for the potential confounders of infant sex and gestational age at delivery. In post hoc analyses we also investigated whether groups differed in the proportion of children with mild (<85) and significant (<70) mental delay. Missing data were multiply imputed using regression models (either normal, poisson or binary) with 50 imputations. Sensitivity analyses were performed using different seeds, increasing the number of imputations or adding further terms to the regression models. The results of these sensitivity analyses were similar to those presented here.

Results

Enrolment for the trial began on Apr. 4, 2001 and ended Oct. 28, 2005. Follow-up commenced on Jan. 17, 2003 and ended Sep. 21, 2007. Adequate data for the analysis of the primary outcome were available on 614 infants, 93.5% of the infants who were originally enrolled in the trial (92.5% in the high-DHA group and 94.3% in the standard-DHA group). The demographic and clinical characteristics of the infants and their families at randomization were comparable between the two groups (see Table 1).

Median duration of treatment was comparable between the high-DHA (9.4 weeks, inter-quartile range, IQR 7.9 to 11.4 weeks) and the standard-DHA (9.4 weeks, IQR 8.0 to 11.6 weeks) groups. Maternal compliance based on capsule returns was 81.1% in the high-DHA group and 81.7% in the standard-DHA group (p=0.88). Mean DHA (±SD) concentration in the milk of women in the high-DHA group was greater than standard treatment (0.85±0.39% vs. 0.25±0.13% total fatty acids, p<0.0001) as was the mean DHA concentration in the three batches of preterm formula used for the trial (1.11±0.29% vs. 0.42±0.05% total fatty acids, p<0.0001). The mean AA (±SD) concentration did not differ between groups for human milk (0.41±0.09% vs. 0.40±0.09% total fatty acids) or preterm infant formula (0.69±0.29% vs. 0.69±0.22% total fatty acids). At the end of dietary treatment 72% of women in the high-DHA group correctly guessed their group allocation as indicated by more frequent reports of fishy eructations from the high-DHA group compared with standard treatment (140/322 vs. 24/335, unadjusted relative risk 6.20, 95% confidence interval, CI, 3.79 to 10.20, p<0.0001). There were no differences between the groups in maternal report of diarrhea, constipation, nausea or vomiting.

The primary outcome of mean Bayley MDI did not differ between the high-DHA and standard-DHA groups (mean difference, MD, 1.9, 95% CI, −1.0 to 4.7, unadjusted; MD, 1.6, 95% CI −1.2 to 4.3, adjusted). A priori sub-group analyses based on the randomization strata showed interactions between dietary treatment and sex, and between dietary treatment and birth weight. The MDI of girls fed the high-DHA diet was significantly higher than girls fed the standard-DHA diet in both unadjusted and adjusted analyses (MD, 4.7, 95% CI 0.5 to 8.8 unadjusted; MD, 4.5, 95% CI 0.5 to 8.5 adjusted, Table 2). The MDI of infants born <1250 g and fed a high-DHA diet to EDD was higher than that of infants fed standard-DHA diets in the unadjusted comparison (MD, 4.7, 95% CI 0.2 to 9.2). For Bayley PDI there was no significant difference between groups (MD, 0.9, 95% CI, −1.8 to 3.6). There were no interactions between diet and sex or between diet and birth weight strata and consequently no differences in PDI between the groups in either of the birth weight strata or for boys and girls. At 18 months' corrected age, the degree of social and cognitive stimulation available in the home environment did not differ between groups (HSQ score ±SD, 34±4, n=322 in the high-DHA group vs. 34±3, n=335 in the standard-DHA group).

Post-hoc analyses indicated that overall fewer infants had significantly delayed mental development with high-DHA diets compared with standard DHA. There were fewer infants born <1250 g in the high-DHA group with mildly delayed mental development and fewer infants born ≥1250 g fed the high-DHA diet with significant mental delay compared with the standard-DHA diet.

The secondary clinical outcomes of the infants are shown in Table 2. Blindness and hearing impairment requiring aids were rare. There were no differences in anthropometric measures between the groups except that at 18 months' corrected age infants who were allocated the high-DHA diet were longer than infants allocated to the standard diet (Table 2). The extent of breastfeeding did not differ between groups at EDD (Table 2), 4, 12 or 18 months corrected age. Other secondary outcomes also did not differ between groups, but fewer infants fed high-DHA in the preterm period required oxygen treatment at 36 weeks compared with standard DHA treatment after correction for gestational age at birth and sex (Table 2). There were two maternal deaths after the end of the intervention phase (suicide by hanging and Wolff Parkinson White Syndrome with secondary substance abuse) in the standard-DHA group.

Impacts of the high-DHA and standard-DHA diet on various allergy indicators was also assessed at 12 or 18 months corrected age. As shown in Table 3, reductions in the incidence of hayfever, asthma and eczema were all observed in infants on the high-DHA diet. The reduction in hayfever incidence was of particular significance (p-value=0.03), and when analysed more closely the reductions were found to be most dramatic in boys (1.6% on high-DHA compared to 10.9% on standard-DHA; p=0.01).

REFERENCES

1. Makrides M., Neumann M. A., Gibson R. A. Effect of maternal docosahexaenoic acid (DHA) supplementation on breast milk composition. Eur J Clin Nutr. 1996; 50(6): 352-357.
2. Bayley N. Manual for the Bayley Scales of Infant Development, Second Edition (BSID-II). San Antonio, Tex.: Psychological Corporation; 1993.
3. Lucas A., Morley R., Cole T. J., Lister G., Leeson-Payne C. Breast milk and subsequent intelligence quotient in children born preterm. Lancet. 1992; 339(8788): 261-264.
4. Frankenburg W. K., Coons C. E. Home Screening Questionnaire: its validity in assessing home environment. J Pediatr. 1986; 108(4): 624-626.
5. Liang K-Y., Zeger S. L. Longitudinal data analysis using generalized linear models. Biometrika. 1986; 73(1): 13-22.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the invention without departing from the spirit or scope of the invention as broadly described. The present embodiments are therefore to be considered in all respects as illustrative and not restrictive.

TABLE 1

Baseline Demographic and Clinical Characteristics of Children and their Families

| Characteristic | High-DHA (n = 322) | Standard-DHA (n = 335) |
|---|---|---|
| Recruitment Hospital | | |
| Flinders Medical Centre | 31 (9.6) | 32 (9.6) |
| King Edward Memorial Hospital | 65 (20.2) | 57 (17.0) |
| Royal Brisbane & Women's Hospital | 46 (14.3) | 50 (14.9) |
| Royal Women's Hospital | 61 (18.9) | 63 (18.8) |
| Women's & Children's Hospital | 119 (37.0) | 133 (39.7) |
| Mother's Age at Trial Entry (years) | 29.9 (5.8) | 30.2 (5.4) |
| Mother Completed Secondary Education | 205 (63.7) | 201 (60.1) |
| Father Completed Secondary Education | 172 (53.5) | 188 (56.0) |
| Mother Smoked During Pregnancy | 82 (25.6) | 84 (25.1) |
| Previous PreTerm Births | 51 (15.8) | 58 (17.4) |
| Birth by Caesarean Section | 220 (68.3) | 235 (70.0) |
| Antenatal Steroids Administered | 279 (86.6) | 302 (90.1) |
| Multiple Pregnancy | 98 (30.4) | 123 (36.7) |
| Gestational Age at Birth (weeks) | 30 (27-31) | 30 (27-31) |
| Caucasian | 283 (87.9) | 311 (92.8) |
| Male Sex | 173 (53.7) | 182 (54.3) |
| Birth Weight (g) | 1308 (423) | 1307 (415) |
| Small for gestational age | 61 (18.9) | 62 (18.6) |
| Birth Weight <1250 g | 147 (45.7) | 149 (44.5) |
| Recumbent Length At Birth (cm) | 38.2 (4.0) | 38.1 (4.0) |
| Head Circumference At Birth (cm) | 27.2 (2.8) | 27.3 (2.7) |
| Days of Partial Enteral Feeds Pre-Randomization | 2 (1-4) | 2 (0-3) |
| Infant Age at Randomization (days) | 4 (3-6) | 4 (2-5) |
| Infants Receiving Breast Milk at Trial Entry | 297 (92.2) | 306 (91.3) |

TABLE 1-continued

Baseline Demographic and Clinical Characteristics of Children and their Families

| Characteristic | High-DHA (n = 322) | Standard-DHA (n = 335) |
|---|---|---|

Values are number (%) of babies, mean (sd) or median (interquartile range)

TABLE 2

Secondary Clinical Outcomes

|  | High-DHA | Standard-DHA | Unadjusted Effect (95% CI) | Unadjusted P-value | Adjusted Effect (95% CI) | Adjusted P-value |
|---|---|---|---|---|---|---|
| All | n = 322 | n = 335 |  |  |  |  |
| Death | 9 (2.8) | 9 (2.7) | 1.04 (0.42, 2.59) | 0.93 | 1.09 (0.44, 2.66) | 0.86 |
| Pre-Discharge Death | 9 (2.8) | 6 (1.8) | 1.56 (0.56, 4.34) | 0.39 | 1.66 (0.63, 4.41) | 0.31 |
| Days In NICU | 22 (3-31) | 21 (4-33) | 1.02 (0.82, 1.27) | 0.87 | 1.03 (0.88, 1.20) | 0.75 |
| Days In Hospital Care | 64 (40-80) | 64 (41-80) | 1.01 (0.92, 1.10) | 0.87 | 1.00 (0.95, 1.06) | 0.92 |
| Days On Parenteral Nutrition | 12 (5-15) | 12 (5-14) | 1.06 (0.90, 1.24) | 0.52 | 1.03 (0.92, 1.16) | 0.59 |
| Days Of Intravenous Lipids | 8 (0-12) | 8 (0-10) | 1.06 (0.85, 1.32) | 0.59 | 1.06 (0.87, 1.30) | 0.54 |
| Days Until Full Enteral Feeds | 12 (6-14) | 12 (6-14) | −0.2 (−2.0, 1.6) | 0.82 | −0.2 (−1.0, 0.6) | 0.55 |
| Exclusively Human Milk Fed at EDD | 142 (44.1) | 135 (40.2) | 1.10 (0.87, 1.39) | 0.42 | 1.11 (0.88, 1.40) | 0.39 |
| Feeding Interrupted | 106 (32.9) | 106 (31.6) | 1.04 (0.82, 1.32) | 0.74 | 1.07 (0.87, 1.31) | 0.55 |
| Any NEC | 14 (4.3) | 7 (2.1) | 2.06 (0.83, 5.13) | 0.12 | 2.14 (0.87, 5.22) | 0.10 |
| Bowel Surgery | 12 (3.7) | 9 (2.7) | 1.39 (0.58, 3.33) | 0.46 | 1.45 (0.63, 3.35) | 0.39 |
| Oxygen Treatment at 36 weeks | 60 (18.6) | 84 (25.1) | 0.74 (0.54, 1.02) | 0.07 | 0.76 (0.58, 1.00) | 0.05 |
| Any Intraventricular Haemorrhage | 45 (14.0) | 44 (13.2) | 1.06 (0.71, 1.59) | 0.77 | 1.07 (0.72, 1.58) | 0.73 |
| Severe Intraventricular Haemorrhage[a] | 9 (2.8) | 6 (1.8) | 1.56 (0.56, 4.33) | 0.39 | 1.63 (0.61, 4.33) | 0.33 |
| Any Retinopathy of Prematurity | 74 (23.0) | 73 (21.8) | 1.05 (0.77, 1.45) | 0.74 | 1.09 (0.85, 1.40) | 0.49 |
| Severe Retinopathy of Prematurity[b] | 14 (4.3) | 17 (5.1) | 0.86 (0.42, 1.75) | 0.67 | 0.91 (0.46, 1.80) | 0.79 |
| Any Sepsis | 53 (16.6) | 48 (14.3) | 1.16 (0.79, 1.69) | 0.46 | 1.18 (0.85, 1.65) | 0.32 |
| Postnatal steroids | 30 (9.3) | 34 (10.2) | 0.92 (0.56, 1.51) | 0.73 | 0.96 (0.61, 1.50) | 0.85 |
| Small for gestational age at EDD | 109 (33.8) | 105 (31.4) | 1.08 (0.85, 1.37) | 0.53 | 1.09 (0.86, 1.37) | 0.49 |
| Weight at EDD (g) | 3175 (553) | 3129 (535) | 42 (−118, 203) | 0.60 | 42 (−116, 199) | 0.60 |
| Weight at 18 Months (g) | 11625 (1811) | 11277 (1588) | 201 (−237, 639) | 0.37 | 187 (−250, 623) | 0.40 |
| Length at EDD (cm) | 48.7 (3.3) | 48.4 (3.3) | 0.2 (−0.3, 0.8) | 0.42 | 0.2 (−0.3, 0.8) | 0.45 |
| Length at 18 Months (cm) | 82.8 (5.2) | 81.7 (4.7) | 0.9 (0.2, 1.7) | 0.01 | 0.9 (0.2, 1.6) | 0.01 |
| Head circumference at EDD (cm) | 35.4 (1.8) | 35.4 (1.9) | 0.10 (−0.6, 0.7) | 0.85 | 0.10 (−0.6, 0.7) | 0.85 |
| Head circumference at 18 Months (cm) | 47.6 (2.5) | 47.6 (2.2) | −0.06 (−0.8, 0.7) | 0.86 | −0.05 (−0.8, 0.7) | 0.88 |
| Seizures at 18 months | 7 (2.0) | 17 (5.2) | 0.39 (0.15, 1.04) | 0.06 | 0.39 (0.15, 1.04) | 0.06 |
| Unilateral or bilateral blindness at 18 months | 0 | 1 (0.3) | — | — | — | — |
| Severe hearing loss requiring aids at 18 months | 0 | 1 (0.3) | — | — | — | — |
| Cerebral Palsy at 18 months | 13 (3.9) | 10 (3.0) | 1.31 (0.56, 3.06) | 0.53 | 1.31 (0.56, 3.06) | 0.53 |

Values are number of babies (%) with effect being Relative Risk or mean (interquartile range) with Ratio of Means as effect Adjusted for GA at delivery and sex. Further adjustment for pilot phase vs multi-centre phase did not alter the results.
[a]Grade 3 or 4
[b]Grade 3 or higher

TABLE 3

Allergy diagnosis at 12 or 18 months corrected age

|  | High-DHA | Standard-DHA |  |
|---|---|---|---|
| Hayfever | 3.5% | 8.6% | (p = 0.03) |
| Hayfever (boys) | 1.6% | 10.9% | (p = 0.01) |
| Hayfever (girls) | 5.7% | 5.6% |  |
| Asthma | 19.8% | 21.0% |  |
| Eczema | 25.8% | 27.0% |  |

What is claimed is:

1. A method for promoting the neurological development of a preterm infant, the method comprising administration to the preterm infant of DHA in an amount of at least 62 mg/kg of body weight per day.

2. The method of claim 1, comprising administration to the infant of DHA in an amount of at least about 80 mg/kg of body weight per day.

3. The method of claim 2, comprising administration to the infant of DHA in an amount of at least about 90 mg/kg of body weight per day.

4. The method of claim 1, wherein the infant is a female infant.

5. The method of claim 1, wherein the infant is born prior to 33 weeks gestation.

6. The method of claim 1, wherein the infant is born prior to 36 weeks gestation.

7. The method of claim 1, wherein the administration is continued until the infant reaches term corrected age.

8. The method of claim 1, wherein the infant is classified as small for gestational age.

9. The method of claim 1, wherein the infant has a birth weight of less than or equal to about 1250 g.

10. The method of claim 1, wherein the administration commences within about 24 hours of the birth of the infant.

11. The method of claim 1, wherein the administration commences at a time when the infant commences enteral feeding.

12. The method of claim 1, wherein the administration is enteral or parenteral administration.

13. The method of claim 1, wherein the DHA is administered to the infant in combination with a source of protein.

14. The method of claim 1, wherein the DHA is administered to the infant in combination with vitamins and/or minerals.

15. The method of claim 1, wherein the DHA is administered to the infant in combination with one or more of the following: human milk, infant formula and human milk fortifier.

16. The method of claim 1, wherein the DHA is administered in the form of an emulsion.

17. The method of claim 1, wherein the infant is in utero.

18. The method of claim 17, wherein the administration commences when the infant is in utero and continues after birth of the infant.

19. The method of claim 17, wherein the infant's mother has been identified as being at risk of giving birth to the infant preterm, or at risk of giving birth to an infant that will be classified as small for gestational age.

20. A method for promoting the neurological development of a preterm infant, the method comprising administration to the preterm infant of fatty acids including DHA, wherein the DHA represents about 1% or more of the fatty acids.

21. The method of claim 20, wherein the DHA is present in an amount of more than 1% of the fatty acids.

22. The method of claim 21, wherein the DHA is present in an amount between more than 1% and about 30% of the fatty acids.

23. The method of claim 20, wherein the infant is a female infant.

24. The method of claim 20, wherein the infant is born prior to 33 weeks gestation.

25. The method of claim 20, wherein the infant is born prior to 36 weeks gestation.

26. The method of claim 20, wherein the administration is continued until the infant reaches term corrected age.

27. The method of claim 20, wherein the infant is classified as small for gestational age.

28. The method of claim 20, wherein the infant has a birth weight of less than or equal to about 1250 g.

29. The method of claim 20, wherein the administration commences within about 24 hours of the birth of the infant.

30. The method of claim 20, wherein the administration commences at a time when the infant commences enteral feeding.

31. The method of claim 20, wherein the administration is enteral or parenteral administration.

32. The method of claim 20, wherein the DHA is administered to the infant at least once a day.

33. The method of claim 32, wherein the DHA is administered to the infant at least three times a day.

34. The method of claim 33, wherein the DHA is administered to the infant at least five times a day.

35. The method of claim 20, wherein the DHA is administered to the infant in combination with a source of protein.

36. The method of claim 20, wherein the DHA is administered to the infant in combination with vitamins and/or minerals.

37. The method of claim 20, wherein the DHA is administered to the infant in combination with one or more of the following: human milk, infant formula and human milk fortifier.

38. The method of claim 20, wherein the DHA is administered in the form of an emulsion.

39. The method of claim 20, wherein the infant is in utero.

40. The method of claim 39 wherein the administration commences when the infant is in utero and continues after birth of the infant.

41. The method of claim 40, wherein the infant's mother has been identified as being at risk of giving birth to the infant preterm, or at risk of giving birth to an infant that will be classified as small for gestational age.

42. The method of claim 1, wherein the infant is at risk of delayed neurological development.

43. The method of claim 20, wherein the infant is at risk of delayed neurological development.

44. The method of claim 42, wherein neurological development is assessed by the Bayley Mental Development Index (MDI).

45. The method of claim 43, wherein neurological development is assessed by the Bayley Mental Development Index (MDI).

* * * * *